United States Patent [19]

Kelley

[11] Patent Number: 4,880,812

[45] Date of Patent: Nov. 14, 1989

[54] PYRIMIDINE COMPOUNDS

[75] Inventor: James L. Kelley, Raleigh, N.C.

[73] Assignee: Burroughs Wellcome Co., Research Triangle Park, N.C.

[21] Appl. No.: 109,225

[22] Filed: Oct. 16, 1987

[30] Foreign Application Priority Data

Oct. 18, 1986 [GB] United Kingdom ............... 8625019

[51] Int. Cl.$^4$ ................ A61K 31/505; C07D 239/49; C07D 239/36
[52] U.S. Cl. ................................. 514/272; 514/16; 514/17; 514/18; 514/19; 530/331; 530/330; 530/329; 544/321; 260/998.2
[58] Field of Search .............. 260/998.2; 544/321; 530/331; 514/272, 17

[56] References Cited

FOREIGN PATENT DOCUMENTS

0239362A2  9/1987  European Pat. Off. .
0268377    5/1988  European Pat. Off. .

OTHER PUBLICATIONS

Chemische Berichte, vol. 110, No. 4, 1977, pp. 1462–1469, F. Seela, et al: Mannich-Reaktion AM 2-Amino-3,7-Dihydropyrrolo (2,3-d-)-Pyrimidin-4-ON, dem Chromophor des Ribonucleosids 'Q'.
Khim Farm. ZH., vol. 1, No. 6, 1967, pp. 5–9, V. M. Berezovskij, et al, Synthesis pyrimidine Analogs of Folic Acid.
J. of Pharm. Sci., vol. 52, No. 9, Sep. 1963, pp. 840–843, B. R. Baker, et al, Analogs of Tetrahydrofolic Acid VII, Synthesis of N-(1-(2-amino-4-hydroxy-6-methyl-5-pyrimidil)-3propyl)-p-aminobenzoyl-L--glutamic acid, an inhibitor of folic reductase.
J. of Medicinal Chem., vol. 6, Nov. 1963, pp. 664–669, B. R. Baker, et al, Analogs of Tetrahydrofolic Acid. IX, Synthesis of N-(1-(2-amino-4-hydroxy-6--phenyl-5-pyrimidyl)-3-propyl)-p-aminobenzoyl-L--glutamic acid, a nonclassical' inhibitor of some folic cofactor area enzymes.
Chemical Abstracts, vol. 68, no. 11, (1968), p. 4797, col. 1, abstract no. 49546a, Columbus, Ohio, U.S..

Primary Examiner—John M. Ford
Attorney, Agent, or Firm—Donald Brown

[57] ABSTRACT

The present invention provides a compound of formula (I):

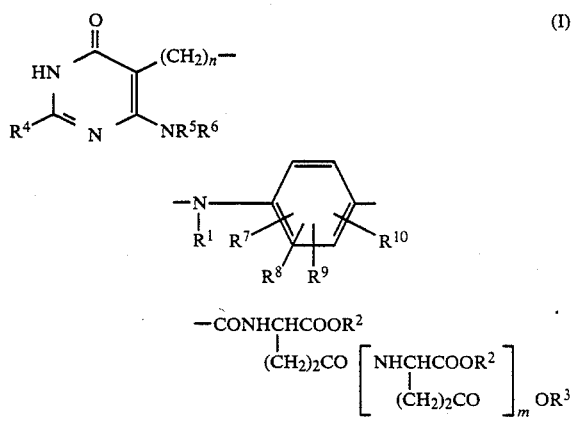

wherein $R^1$ is hydrogen, $C_{1-4}$ alkyl, acetyl or formyl; $R^2$ and $R^3$ are the same or different and are hydrogen or $C_{1-4}$ alkyl; $R^4$ is $NR^{11}R^{12}$; $R^{11}$, $R^{12}$, $R^5$ and $R^6$ are the same or different and are hydrogen, $C_{1-4}$ alkyl or $C_{1-12}$ acyl; $R^7$, $R^8$, $R^9$ and $R^{10}$ are the same or different and are hydrogen, halo, $C_{1-4}$ haloalkyl, $C_{1-4}$ alkyl and $C_{1-4}$ alkoxy; and n is 2, 3, 4 or 5; m is 0 or an integer from 1 to 6; or a salt thereof, methods for the preparation of the compounds of the formula (I), intermediates in their preparations, pharmaceutical formulations containing them, and their use in the treatment of tumors.

13 Claims, No Drawings

PYRIMIDINE COMPOUNDS

The present invention relates to a class of novel glutamic acids, acid esters and salts, processes and intermediates for their preparation, pharmaceutical formulations containing them, and to their use in medicine and agriculture.

A structurally distinct class of novel substituted glutamic acids and acid esters had now been discovered in which the glutamic acid or acid ester is substituted by a pyrimidylalkylaminobenzoyl chain characterized in that the pyrimidyl moiety is 2,4-diamino-1,6-dihydro-6-oxo-5-pyrimidinyl. They have, moreover, been found to possess anti-neoplastic activity in that the compounds are able to inhibit the unregulated multiplication and proliferation of undifferentiated cells. Such activity has been demonstrated against lymphocytic and connective tissue cells in the lymphocytic leukemia P388/0 and the cell culture cytotoxicity tests, both of which are described hereinafter.

Accordingly, the present invention provides a compound of formula (I):

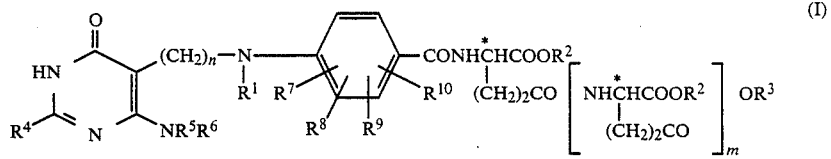

wherein $R^1$ is hydrogen, $C_{1-4}$ alkyl, acetyl or formyl; $R^2$ and $R^3$ are the same or different and are hydrogen or $C_{1-4}$ alkyl; $R^4$ is $NR^{11}R^{12}$; $R^{11}$, $R^{12}$, $R^5$ and $R^6$ are the same or different and are hydrogen, $C_{1-4}$ alkyl or $C_{1-12}$ acyl; $R^7$, $R^8$, $R^9$ and $R^{10}$ are the same or different and are hydrogen, halo, $C_{1-4}$ haloalkyl, $C_{1-4}$ alkyl and $C_{1-4}$ alkoxy; and n is 2, 3, 4 or 5; m is 0 or an integer from 1 to 6; or a salt thereof.

Examples of $R^1$, when $C_{1-4}$ alkyl, include methyl. It is however, preferred that $R^1$ is hydrogen or formyl.

Examples of $R^2$ and $R^3$, when $C_{1-4}$ alkyl, include methyl and ethyl. It is, however, preferred that $R^2$ and $R^3$ are both hydrogen.

Preferably, n is 3.
Suitably m is 0 to 2.
Preferably, m is 0

The compounds of the present invention have an asymmetric carbon atom indicated by the asterisk in formula (I) and are, therefore, capable of existing as optical isomers. Although all such isomers, individually and as mixtures, are included within the scope of the present invention, the L-optical isomers are preferred.

Of the compounds exemplified hereinafter, those that are preferred include the compound of Example 1.

As salts of the compounds of the present invention, there are included acid addition salts derived from either of the two terminal amino groups that substitute the pyrimidyl moiety or from the amino group present in the chain between the phenylene and the —(CH₂)ₙ— moieties and salts comprising an anionic species derived from a compound of formula (I), wherein one or both of $R^2$ and $R^3$ is or are hydrogen, and a cation. In both types of salts, the anti-neoplastic activity resides in the moiety derived from the compound of the invention as defined herein and the identity of the other component is of less importance although for therapeutic and prophylactic purposes it is, preferably, pharmaceutically acceptable to the patient. Examples of pharmaceutically acceptable acid addition salts include those derived from mineral acids, such as hydrochloric, hydrobromic, phosphoric, metaphosphoric, nitric and sulphuric acids, and organic acids, such as tartaric, acetic, citric, malic, lactic, fumaric, benzoic, glycollic, gluconic, succinic and arylsulphonic, for example p-toluenesulphonic, acids. Examples of salts comprising an anionic species derived from a compound of formula (I), wherein one or both of $R^2$ and $R^3$ is or are hydrogen, and a cation include ammonium salts, alkali metal salts, such as sodium and potassium salts, alkaline earth salts, such as magnesium and calcium salts, and salts formed with organic bases, for example, amino salts derived from mono-, di- or tri-(lower alkyl) or (lower alkanol)amines, such as triethanolamine and diethylaminoethylamine, and salts with heterocyclic amines such as piperidine, pyridine, piperazine and morpholine. The pharmaceutically acceptable salts together with the salts which are not thus acceptable have utility in the isolation and/or the purification of the compounds of the invention, and the pharmaceutically unacceptable salts are also useful in being convertible to the pharmaceutically acceptable salts by techniques well known in the art.

The present invention also provides a process for the preparation of a compound of formula (I), as defined herein, or a salt thereof, which comprises deacylating a compound of formula (II):

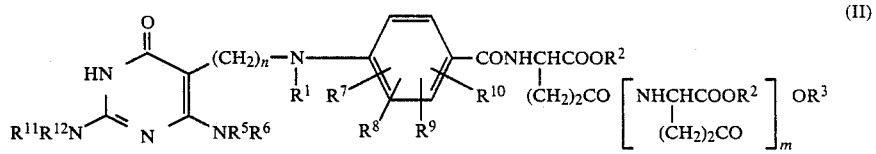

wherein $R^1$ is hydrogen or $C_{1-4}$ alkyl; $R^2$, $R^3$, $R^7$, $R^8$, $R^9$ and $R^{10}$ and n and m are as defined above in formula (I); one of the groups $R^5$, $R^6$, $R^{11}$ and $R^{12}$ being $C_{1-12}$ acyl, the other groups $R^5$, $R^6$, $R^{11}$ and $R^{12}$ being the same or different and are hydrogen or $C_{1-12}$ acyl, and optionally thereafter (i) in the case where, in the resulting compound of formula (I) $R^1$ is hydrogen, formylating the compound so as to prepare the corresponding compound of formula (I), wherein $R^1$ is formyl; and/or (ii) converting $R^2$, $R^3$, $R^5$, $R^6$, $R^{11}$ and $R^{12}$ in the resulting compound of formula (I) into another $R^2$, $R^3$, $R^5$, $R^6$, $R^{11}$ and $R^{12}$, and optionally forming a salt.

Preferably, $R^5$, $R^6$, $R^{11}$ and $R^{12}$, when $C_{1-12}$ acyl, are carboxylic $C_{1-12}$ acyl. Most preferably, $R^5$, $R^6$, $R^{11}$ and $R^{12}$, when $C_{1-12}$ acyl, are the same or different and are $C_{1-12}$ carboxylic acyl, in particular $C_{1-6}$ alkanoyl, especially acetyl.

The deacylation of a compound of formula (II) may be carried out conventionally. In the preferred case where $R^5$, $R^6$, $R^{11}$ and $R^{12}$, when $C_{1-12}$ acyl, are the same or different and are $C_{1-6}$ alkanoyl, the deacylation is, preferably, carried out at an elevated temperature in an alcoholic solvent, such as ethanol or ethanol containing a small amount of 2-mercaptoethanol so as to prevent any oxidation of the resulting compound of formula (I), in the presence of a base, such as sodium hydroxide. In the event that one or both of $R^2$ and $R^3$ in the compound of formula (II) is or are $C_{1-4}$ alkyl, then the conditions preferred for deacylation are also likely to lead to deesterification. In such circumstances, the product of the deacylation is a compound of formula (I), wherein $R^2$ and $R^3$ are both hydrogen. In order, therefore, to prepare a compound of formula (I), wherein one or both of $R^2$ and $R^3$ is or are $C_{1-4}$ alkyl, the resulting compound of formula (I), wherein $R^2$ and $R^3$ are both hydrogen, is esterified as described hereinafter.

The optional formylation of the resulting compound of formula (I), wherein $R^1$ is hydrogen, is, preferably, carried out by reacting the compound with acetic formic anhydride at an elevated temperature.

Examples of the optional conversion of $R^2$ and/or $R^3$ in the resulting compound of formula (I) into another $R^2$ and/or $R^3$ include the optional conversion of hydrogen into $C_{1-4}$ alkyl using conventional esterification reagents and conditions, for example a $C_{1-4}$ alkanol in the presence of an acid. This may be a useful optional conversion to carry out in the event that, in the preparation of a compound of formula (I), wherein one or both of $R^2$ and $R^3$ is or are $C_{1-4}$ alkyl, the compound undergoes deesterification as described hereinbefore. In such circumstances, the desired ester may be prepared from the free acid as just described.

The optional formation of a salt of a compound of formula (I) may be carried out conventionally.

The compounds of formula (II) may be prepared by reducing a mixture of a compound of formula (III):

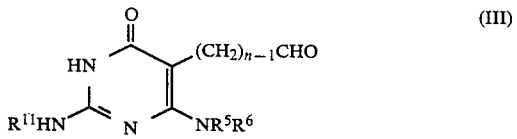

wherein $R^5$, $R^6$, $R^{11}$ and $n$ are as defined herein, and a compound of formula (VI):

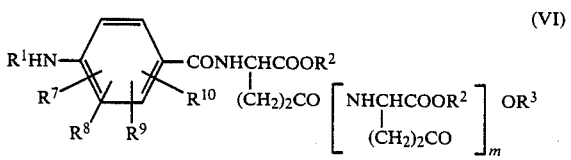

wherein $R^1$, $R^2$, $R^3$, $R^7$, $R^8$, $R^9$ and $R^{10}$ are as defined herein; and, in the case where, in the resulting compound of formula (II) $R^1$ is hydrogen, optionally alkylating the compound so as to prepare the corresponding compound of formula (II), wherein $R^1$ is $C_{1-4}$ alkyl.

The reduction of a mixture of the compounds of formulae (III) and (VI) may be carried out in accordance with conventional reductive alkylation reactions. It is, however, preferred that the reduction is effected with sodium cyanoborohydride in a solvent in the presence of an acid, such as acetic acid which may also function as the solvent.

The optional alkylation of the resulting compound of formula (II), wherein $R^1$ is hydrogen, is, preferably, carried out by reductive alkylation in which a mixture of the compound of formula (II) and a $C_{1-4}$ aldehyde are reduced with sodium cyanoborohydride in the presence of an acid, such as acetic acid.

The compounds of formula (II), wherein $n$ is 3, may also, although less preferably, be prepared by reducing a mixture of a compound of formula (IV):

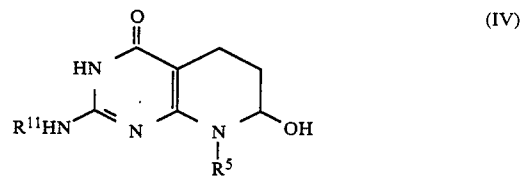

wherein $R^5$ and $R^{11}$ are as defined herein, and a compound of formula (VI) as defined herein; and, in the case where, the resulting compound of formula (II) where $R^1$ is hydrogen, optionally alkylating the compound so as to prepare the corresponding compound of formula (II), wherein $R^1$ is $C_{1-4}$ alkyl.

The reduction of a mixture of the compounds of formulae (IV) and (VI) may be carried out analogously to the reduction of a mixture of the compounds of formulae (III) and (VI) in which sodium cyanoborohydride is used in the presence of an acid, such as acetic acid, to effect the reduction. It is, however, preferred, in the reduction of the mixture of the compounds of formulae (VI) and (IV), that acetic acid is not used also as the solvent but that, for example, methanol or a mixture of methanol and 2-methoxyethanol is used in this regard. It is also preferred that the reduction is carried out in the presence of a dehydrating agent, such as molecular sieves.

The optional alkylation of the resulting compound of formula (II), wherein $R^{11}$ is hydrogen, may be carried out as described hereinbefore.

The compounds of formulae (III) and (IV) may both be prepared by hydrolysis of a compound of formula (V):

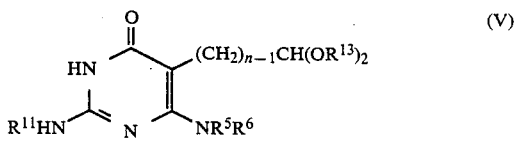

wherein $R^{11}$, $R^5$, $R^6$ and $n$ are as defined herein and $R^{13}$ is $C_{1-4}$ alkyl, such as ethyl.

In the case of the preparation of a compound of formula (III), the hydrolysis may be carried out in a solvent, such as dichloromethane or acetone, in the presence of an acid, such as oxalic acid or 4-toluenesulphonic acid. In addition, in the case of the preparation of a compound of formula (III), wherein $n$ is 3, the hydrolysis may also be carried out simply in water at room or a slightly elevated temperature.

In the case of the preparation of a compound of formula (IV), the hydrolysis is carried out with a compound of formula (V), wherein n is 3, and may be achieved simply in boiling or nearly boiling water.

The compound of formula (V) may be prepared by acylating a compound of formula (VII):

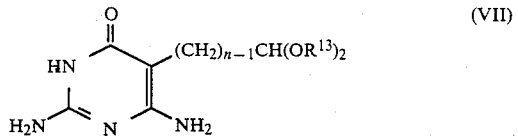

wherein $R^{13}$ and n are as defined herein.

The acylation of a compound of formula (VII) may be carried out conventionally using, for example, an acid anhydride in the presence of a base, such as pyridine.

The compound of formula (VII) may be prepared by reacting a compound of formula (VIII):

wherein $R^{13}$ and n are as defined herein and $R^{14}$ is $C_{1-4}$ alkyl, such as ethyl, and guanidine.

The reaction between the compound of formula (VIII) and guanidine may be carried out conventionally, for example, in a solvent, such as ethanol, in the presence of a base, such as sodium methoxide, at an elevated temperature.

The compound of formula (VIII) may be prepared by reacting a compound of formula (IX):

wherein $R^{14}$ is as defined herein, and a compound of formula (X):

wherein $R^{13}$ and n are as defined herein and L is a leaving group, such as chloro, bromo, iodo or tosyloxy.

The reaction between the compounds of formulae (IX) and (X) may be carried out conventionally, for example, in a solvent, such as ethanol, in the presence of a base, such as sodium methoxide.

The compounds of formulae (VI), (IX) and (X) are commercially available, or may be obtained by carrying out a published process for their preparation, or by carrying out a process analogous to a published process for the preparation of structurally analogous compounds. For example, the compounds of formula (VI) may be obtained by using the process described in *J. Am. Chem. Soc.*, 1958, 80, page 5778 et seq.

Compounds of the formula (I) where m is 1 or 2 may be prepared enzymatically from the corresponding compound of the formula (I) where m is 0 by reaction with glutamic acid in the presence of a suitable enzyme, such as *E. coli* folylpoly-γ-glutamate synthetase.

While it is possible for the compounds or salts of the present invention to be administered as the raw chemical, it is preferred to present them in the form of a pharmaceutical formulation. Accordingly, the present invention further provides a pharmaceutical formulation, for medicinal application, which comprises a compound of the present invention or a pharmaceutically acceptable salt thereof, as hereinbefore defined, and a pharmaceutically acceptable carrier therefor.

The pharmaceutical formulation may optionally contain other therapeutic agents that may usefully be employed in conjunction with the compound or salt of the present invention, for example a dihydrofolate reductase inhibitor that is capable of enhancing the antineoplastic activity of the compounds and salts of the present invention. The expression "pharmaceutically acceptable" as used herein in relation to the carrier is used in the sense of being compatible with the compound or salt of the invention employed in the formulation and with any other therapeutic agent that may be present, and not being detrimental to the recipient thereof. The carrier itself may constitute one or more excipients conventionally used in the art of pharmacy that enable the compound or salt of the present invention and any other therapeutic agent that may be present, to be formulated as a pharmaceutical formulation.

The pharmaceutical formulations of the present invention include those suitable for oral, parenteral (including subcutaneous, intradermal, intramuscular and intravenous) and rectal administration although the most suitable route will probably depend upon, for example, the condition and identity of the recipient. The formulations may conveniently be presented in unit dosage form and may be prepared by any of the methods well known in the art of pharmacy. All methods include the step of bringing into association the active ingredient, i.e., the compound or salt of the present invention, with the carrier. In general, the formulations are prepared by uniformly and intimately bringing into association the active ingredient with a liquid carrier or, a finely divided solid carrier or both, and then, if necessary, forming the associated mixture into the desired formulation.

The pharmaceutical formulations of the present invention suitable for oral administration may be presented as discrete units, such as a capsule, cachet, tablet, or lozenge, each containing a predetermined amount of the active ingredient; as a powder or granules; as a solution or a suspension in an aqueous liquid or a non-aqueous liquid such as a syrup, elixir or a draught, or as an oil-in-water liquid emulsion or a water-in-oil liquid emulsion. The formulation may also be a bolus, electuary or paste.

Generally, a tablet is the most convenient pharmaceutical formulation suitable for oral administration. A table may be made by compressing or moulding the active ingredient with the pharmaceutically acceptable carrier. Compressed tablets may be prepared by compressing in a suitable machine the active ingredient in a free-flowing form, such as a powder or granules, in admixture with, for example, a binding agent, an inert diluent, a lubricating agent, a disintegrating agent and/or a surface active agent. Moulded tablets may be prepared by moulding in a suitable machine a mixture of the powdered active ingredient moistened with an inert liquid diluent. The tablets may optionally be coated or scored and may be formulated so as to provide slow or controlled release of the active ingredient.

The pharmaceutical formulations of the present invention suitable for parenteral administration include aqueous and non-aqueous sterile injection solutions which may contain, for example, an anti-oxidant, a buffer, a bacteriostat and a solution which renders the composition isotonic with the blood of the recipient, and aqueous and non-aqueous sterile suspensions which may contain, for example, a suspending agent and a thickening agent. The formulations may be presented in unit-dose or multi-dose containers, for example sealed ampoules and vials, and may be stored in a freeze-dried (lyophilized) condition requiring only the addition of the sterile liquid carrier, for example water for injection, immediately prior to use.

Extemporaneous injection solutions and suspensions may be prepared from sterile powders, granules and tablets of the kind previously described.

The pharmaceutical formulations of the present invention suitable for rectal administration may be presented as a suppository containing, for example, cocoa butter and polyethylene glycol.

As mentioned hereinbefore, the compounds and salts of formula (I) have anti-neoplastic activity as demonstrated hereinafter in the lymphocytic leukemia P388/0 in animals, e.g., mice and the cell culture cytotoxicity tests, in which a representative number of the compounds of the present invention is shown to be active against particular lymphocytic and connective tissue cell lines. It has thus been established that the compounds of the present invention are able to inhibit neoplastic growth. Therefore, the compounds and salts of the present invention are of use in medicine and in particular in the treatment of neoplastic growth, especially lymphocytic leukemia and malignant tumors such as carcinoma and sarcoma in mammals. Accordingly, the present invention yet further provides a method for the treatment of susceptible malignant tumors and leukemia in an animal, e.g., a mammal, which comprises administering to the animal a therapeutically effective amount of a compound or salt of the present invention. In the alternative, there is also provided a compound or salt of the present invention for use in medicine and in particular for use in the treatment of a neoplastic growth, e.g., leukemia and malignant tumors.

The animal requiring treatment with a compound or salt of the present invention is usually a mammal.

Particular examples of a neoplastic growth requiring treatment include lymphocytic leukemia and malignant tumors.

As mentioned hereinbefore, the antineoplastic activity of the compounds and salts of the present invention may be enhanced by a dihydrofolate reductase inhibitor, for example, 2,4-diamino-6-(2,5-dimethoxybenzyl)-5-methylpyrido[2,3-d]pyrimidine hydrochloride. Therefore, it may be advantageous to employ with the compounds and salts of the present invention a dihydrofolate reductase inhibitor in the treatment of neoplastic growth.

The route by which the compound or salt of the present invention is administered to the animal may be oral, parenteral (including subcutaneous, intradermal, intramuscular, intravenous or rectal). If the compound or salt is presented in the form of a pharmaceutical formulation, which, as mentioned hereinbefore, is preferred, then the actual formulation employed will of course depend on the route of administration elected by the physician or veterinarian. For example, if oral administration is preferred, then the pharmaceutical formulation employed is, preferably, one which is suitable for such a route.

A therapeutically effective amount of a compound or salt of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of the present invention for the treatment of neoplastic growth, in particular lymphocytic leukemia or a malignant tumor, will generally be in the range of 0.5 to 600 mg/kg body weight of recipient (mammal) per day and more usually in the range of 7.0 to 200 mg/kg body weight per day. Thus, for a 70 kg adult mammal, the actual amount per day would usually be from 490 to 14,000 mg and this amount may be given in a single dose per day or more usually in a number (such as two, three, four, five or six) of sub-doses per day such that the total daily dose is the same. An effective amount of a salt of the present invention may be determined as a proportion of the effective amount of the compound per se.

The treatment of neoplastic growth with a compound of the present invention may at times require the administration to the animal of an antidote or rescue agent. Particular examples of such agents include leucovorin, hypoxanthine and 5-aminoimidazole-4-carboxamide ribonucleotide (AICAR), although leucovorin is the most preferred.

The compounds of Examples 1, 2 and 3 described hereinafter have also been found to have activity against the mycoplasma, *Spiroplasma citri*. These compounds are, therefore, useful in the treatment or prophylaxis of citrus plants that are infected with this microorganism. The compounds may be applied to the plants by methods known in the art, such as spraying, dusting, incorporating into the soil or injecting into the plant. The compound of Example 1 has also been found to possess activity against certain bacterial organisms that are unable to synthesize their own folic acid and that, therefore, require preformed folate. These organisms are *Lactobacillus casei* and *Streptococcus faecium*. And together with the compound of Example 3, the compound of Example 1 has further been found to possess some activity against yellow fever virus.

The following examples and biological data are provided in illustration of the present invention and should not be construed as in any way constituting a limitation thereof.

EXAMPLE 1

Preparation of
N-[4-[3-(2,4-diamino-1,6-dihydro-6-oxo-5-pyrimidinyl)-propylamino]benzoyl]-L-glutamic acid via compounds of formulae (III) and (IV)

(a) Preparation of ethyl 2-cyano-5,5-diethoxypentanoate

To a stirred solution of 16.2 g (0.30 mol) of sodium methoxide in 100 ml of absolute ethanol was added 160 ml (170 g, 1.50 mol) of ethyl cyanoacetate. The solution was spin evaporated in vacuo at 40° C. and the residual white solid was dissolved in 200 ml of dry dimethylformamide. To this solution was added 50 ml (50 g, 0.30 mol) of 3-chloropropionaldehyde diethyl acetal and a crystal of sodium iodide, and the solution was heated on a steam bath with magnetic stirring and protection from moisture for 5 hours. The red-brown solution was cooled, poured into 300 ml of ice water and extracted with diethylether (6×200 ml). The organic phase was washed with water (3×50 ml), brine (50 ml) and dried over magnesium suphate. The solution was filtered, spin evaporated in vacuo, and the residue was distilled to give 41.3 g (57%) of a clear liquid, bp 90°–108° (0.05 mm Hg) which was sufficiently pure for the next step. Fractional distillation gave as a main fraction a clear liquid, bp 103°–108° (0.025 mm Hg); NMR (CDCl$_3$)δ1.20 (t, 6H, CH(OCH$_2$CH$_3$)$_2$), 1.31 (t, 3H, CO$_2$CH$_2$CH$_3$), 1.90 (m, 2H, CH$_2$C$\overline{H}$CN), 3.60 (m, 5H, CH(OCH$_2$$\overline{CH_3}$)$_2$+CHCN), 4.2$\overline{4}$ (q, 2H, CO$_2$CH$_2$), 4.51 (t, 1H, $\overline{CH}$(OCH$_2$)$\overline{CH_3}$); IR (film) 2265, 1750, 1450 cm$^{-1}$.

(b) Preparation of 3-(2,4-diamino-1,6-dihydro-6-oxo-5-pyrimidinyl)propionaldehyde diethyl acetal To a solution of 22.0 g (407 mmol) of sodium methoxide in 400 ml of absolute ethanol was added 18.2 g (191 mmol) of guanidine hydrochloride and 46.0 g (189 mmol) of ethyl 2-cyano-5,5-diethoxypentanoate. The mixture was refluxed with stirring for 2.5 hours, stirred at ambient temperature overnight and then neutralized with 15 ml of acetic acid. The salts were removed by filtration and washed with 100 ml of ethanol. The combined filtrate and wash were spin evaporated in vacuo to give an off-white solid which was digested with ethyl acetate and cooled. The solid was collected and washed with ethyl acetate. This material, which contained sodium acetate, was dissolved in 150 ml of 1 N sodium hydroxide and then acidified with stirring to pH 5–6 with 10 ml of acetic acid. The resultant precipitate was collected, washed with 50 ml of cold water (product partly soluble in water) and dried; yield, 29.07 g (60%), mp 178°–181°.

Recrystallization of a portion from ethyl acetate-ethanol gave the analytial sample, mp 177°–178°; TLC (C$_6$H$_6$:EtOH/5:1); NMR (DMSO-d$_6$)δ1.11 (t, 6H, CH$_3$), 1.56 (m, 2H, CH$_2$CH$_2$CH), 2.19 (t, 2H, C$\overline{H_2}$CH$_2$CH), 3.2–3.7 (m, 4H, 2 x OCH$_2$), 4.45 (t, 1H, H), (s, H, NH$_2$, 5.98 (s, 2H, NH$_2$), 9.84 $\overline{(s,}$ 1H, $\overline{HNC}$(O)).

Elemental analysis: Calculated for C$_{11}$H$_{20}$$\overline{N_4}$O$_3$: C, 51.6; H, 7.87; N, 21.9. Found: C, 51.7; H, 7.79; N, 21.7.

(c) Preparation of 3-(2-acetylamino-4-diacetylamino-1,6-dihydro-6-oxo-5-pyrimidinyl) propionaldehyde diethyl acetal A stirred mixture of 7.20 g (28.1 mmol) of 3-(2,4-diamino-1,6-dihydro-6-oxo-5-pyrimidinyl)propionaldehyde diethyl acetal, 30 ml of dry pyridine and 30 ml of freshly distilled acetic anhydride was heated on an oil bath at 90° for 6 hours and then stirred at ambient temperature overnight. Solution occurred within 15 minutes as a mixture of diacetyl and triacetyl pyrimidinone formed; extended reaction was required to obtain only the title compound. The solution was spin evaporated in vacuo to give an oil. Ethyl acetate was added and spin evaporated several times until a solid was obtained. The solid was dispersed in cyclohexane and collected; yield, 8.88 g (82%), mp 126°–137° (one spot on TLC). Recrystallization of a portion from cyclohexane-ethylacetate gave the analytical sample, mp 138°–139° ; TLC (C$_6$H$_6$:EtOH/5:1); NMR (DMSO-d$_6$)δ1.08 (t, 6H, 2CH$_2$CH$_3$), 1.63 (m, 2H, CH$_2$CH$_2$CH), 2.13 (s, 3H, Ac), 2.2$\overline{7}$ (s, 6H, 2Ac), 2.2 (2H, $\overline{CH_2}$CH, superimposed on the acetyl singlets), 3.2–3.7 (m, $\overline{4H}$, 2 x OCH$_2$), 4.42 (t, 1H, CH), 11.87 (br s, 2H, AcNH and HNC(O)).

Elemental analysis: Calculated for C$_{17}$H$_{26}$N$_4$O$_6$: C, 53.4; H, 6.85; N, 14.6. Found: C, 53.7; H, 6.87; N, 14.6.

Route Via Compound of Formula (IV)

(d) Preparation of 2-acetamido-8-acetyl-5,6,7,8-tetrahydro-7-hydroxypyrido[2,3-d]pyrimidin-4(3H)-one 3-(2-Acetylamino-4-diacetylamino-1,6-dihydro-6-oxo-5-pyrimidinyl)propionaldehyde diethyl acetal (25.0 g, 0.66 mol) was heated with 100 ml of water on a steam bath for 4 hours. The solution was filtered hot to remove an insoluble by-product, and the filtrates were spin evaporated in vacuo to a thick syrup. This syrup was successively dissolved in ethanol and then ethylacetate followed by spin evaporation each time to give a solid which was digested with ethyl acetate. The solids were collected and dried; yield, 15.1 g (76%), mp 199°–201° of a cream colored solid which was used without further purification. Recrystallization of a portion from 2-propanol gave the analytical sample, mp 202°–205° ; TLC (C$_6$H$_6$:EtOH/10:1): NMR (DMSO-d$_6$)δ11.75 (br s, 1H, NH), 11.30 (br s, 1H, NH, W$\frac{1}{2}$=5 Hz), 6.15 (d, 1H, J=5.0 Hz, OH), 6.06 (m, 1H, J=2.7 Hz when D$_2$O exchange removed OH C$\overline{H}$), 2.43 (s, 3H, CH$_3$), 2.40–2.10 (m, 2H, pyrimidine-CH$_2$), 2.02–1.42 (m, 2H, CH$_2$CH$_2$CH); $^{13}$ C-FT nmr (DM$\overline{SO}$-d$_6$) ppm: 15.7, 23.9, 27.2, $\overline{72}$.8, 102.2, 147.2, 152.4, 160.4, 171.0, 173.4; MS m/e 266, 248.

Elemental analysis: Calculated for C$_{11}$H$_{14}$N$_4$O$_4$: C, 49.6; H, 5.30; N, 21.04. Found: C, 49.6; H, 5.36; N, 20.35

(e) Preparation of dimethyl N-[4-[3-(2,4-bis-(acetamido)-1,6-dihydro-6-oxo-5-pyrimidinyl)-propylamino]benzoyl]-L-glutamate A mixture of 2.30 g (7.6 mmol) of 2-acetamido-8-acetyl-5,6,7,8-tetra hydro-7-hydroxypyrido[2,3-d]pyrimidin-4(3H)-one, 2.40 g (8.15 mmol) of dimethyl N-(4-aminobenzoyl)-L-glutamate, 5 g of 3A molecular sieves, 150 ml of methanol, and 4 ml of acetic acid was stirred with protection from moisture for 3 hours when "imine" formation was complete. Sodium cyanoborohydride (0.38 g) and 8 ml of acetic acid was added to the reaction. After 15 hours a trace of intermediate "imine" was detected by TLC and an additional 50 mg of sodium cyanoborohydride was added. After 1 hour the reaction was diluted with 500 ml of chloroform and filtered through a Celite pad to remove the insolubles. The chloroform solution was washed with four 50 ml portions of 5% aqueous sodium bicarbonate, two 50 ml portions of water, one 50 ml portion of brine, dried over magnesium sulphate and spin evaporated in vacuo. The resultant foam was triturated with 50 ml of ethyl acetate to give white crystals; yield, 2.75 g (65%), mp 144°–150°. Recrystallization from ethanol gave chromatographically pure material; yield, 1.70 g (40%), mp 135°–142°. An analytically pure sample was obtained from a previous run with mp 140°–143°; TLC: (C$_6$H$_6$:EtOH/10:1); NMR (DMSO-d$_6$)δ11.69 (br s, 2H, 2AcNH) 9.68 (br s, 1H, ring NH), 8.24 (br d, 1H, Ar-CONH), 7.65 (d, 2H, ArH), 6.53 (d, 2H, ArH), 6.17 (br t, 1H, $\overline{CH_2}$NH), 4.39 (m, 1H, CHCO$_2$CH$_3$), 3.63 (s, 3H, CO$_2$CH$_3$), 3.58 (s, 3H, CO$\overline{2}$CH$_3$), 3.01 (m, 2H, CH$_2$NHAr), 2.43 (m, 2H, CH$_2$CO$_2$CH$_3$), 2.1 (4H, pyrimidine —CH$_2$ and CHCH$_2$, masked by AcNH peaks), 2.14 (s, 3H, Ac), 2.01 $\overline{(s,}$ 3H, Ac), 1.72 (m, 2H, CH$_2$CH$_2$CH$_2$).

Elemental analysis: Calculated for C$_{25}$H$_{32}$N$_6$O$_8$.$\frac{1}{2}$ H$_2$O: C, 54.2; H, 6.01; N, 15.2. Found: C, 54.3; H, 5.90; N, 15.3

(f) Preparation of N-[4-[3-(2,4-diamino-1,6-dihydro-6-oxo-5-pyrimidinyl)propylamino]benzoyl]-L-glutamic acid A stirred solution of 1.60 g (2.89 mmol) of dimethyl N-[4-[3-(2,4-bis(acetamido)-1,6-dihydro-6-oxo-5-pyrimidinyl)propylamino]benzoyl]-L-glutamate, 50 ml of ethanol and 100 ml of 1 N sodium hydroxide was heated at 50°–60° for 20 hours. The cooled reaction was spin evaporated in vacuo to 50 ml, cooled, and neutralized to pH 5-6 with concentrated hydrochloric acid. The resultant white precipitate was collected, washed with water, diethylether and dried; yield, 0.86 g (66%) mp (sinter 170°) 198°–202° (eff). Recrystallization from methanol gave the analytical sample; yield, 0.33 g (39%), mp (forms hard foam 180°) 200° (eff); TLC (pyridine:BuOH:H$_2$O/1:1:1); NMR (DMSO-D$_6$)δ8.07 (d, 1H, ArCONH), 7.65 (d, 2H, ArH), 6.54 (d, 2H, ArH), 6.22 (br s, 1H, CH$_2$NH), 5.94 (s, 2H, NH$_2$), 5.75 (s, 2H, NH$_2$), 4.34 (m, 1H, CHCO$_2$H), 3.03 (m, 2H, CH$_2$NHAr), 2.30 (m, 4H, pyrimidine-CH$_2$ and CH$_2$CO$_2$H), 2.03 (m, 2H, CHCH$_2$), 1.58 (m, 2H, CH$_2$CH$_2$CH$_2$).

Elemental analysis: Calculated for C$_{19}$H$_{24}$N$_6$O$_6$.H$_2$O: C, 50.7; H, 5.82; N, 18.7. Found: C, 50.4: H, 5.79; N, 18.6.

Route Via Compound of Formula (III)

(g) Preparation of 3-(2-Acetylamino-4-diacetylamino-1,6-dihydro-6-oxo-5-pyrimidinyl)propionaldehyde Method 1: A solution of 3-(2-acetylamino-4-diacetylamino-1,6-dihydro-6-oxo-5-pyrimidinyl)propionaldehyde diethyl acetal (1.00 g, 2.6 mmol) in distilled water (30 ml) was stirred at room temperature for 18 hours. This solution was extracted with ethyl ether (3×50 ml), and chloroform (5×50 ml). The chloroform extracts were combined, washed with water (25 ml), brine (25 ml), dried (MgSO$_4$) and spin evaporated in vacuo. The residue was recrystallized from chloroform/cyclohexane to yield 0.200 g (25% of theory) of analytically pure 3-(2-acetylamino-4-diacetylamino-1,6-dihydro-6-oxo-5-pyrimidinyl)propionaldehyde quarter hydrate, mp 164°–168° C.

Elemental analysis: Calc for C$_{13}$H$_{16}$N$_4$O$_5$¼H$_2$O (MW 312.803): C, 49.9; H, 5.32; N, 17.9. Found: C, 49.8; H, 5.30; N, 17.6.

Method 2: A solution of 3-(2-acetylamino-4-diacetylamino-1,6-dihydro-6-oxo-5-pyrimidinyl)propionaldehyde diethyl acetal (30.0 g, 78.5 mmol) in distilled water (600 ml) was stirred at 53° C. for 3.5 hours and spin evaporated in vacuo at 45° C. The residue was dissolved in dichloromethane (750 ml), washed with brine (50 ml), dried (MgSO$_4$), and spin evaporated in vacuo to a dry solid.

Recrystallization from acetone gave 16.23 g (67% of theory) of 3-(2-acetylamino-4-diacetylamino-1,6-dihydro-6-oxo-5-pyrimidinyl)propionaldehyde, mp 164°–168° C., which was identical to that prepared by Method 1.

(h) Preparation of N-[4-[3-(2,4-Diamino-1,6-dihydro-6-oxo-5-pyrimidinyl)propylamino]benzoyl]-L-glutamic acid To a solution of 3-(2-acetylamino-4-diacetylamino-1,6-dihydro-6-oxo-5-pyrimidinyl)propionaldehyde (9.30 g, 30.2 mmol) and dimethyl N-(4-aminobenzoyl)-L-glutamate (9.85 g, 33.5 mmol) (R. Koehler, L. Goodman, J. DeGraw, and B. R. Baker, *J. Am. Chem. Soc.*, 80, 5779 (1958) in methanol (175 ml) was added acetic acid (7.7 ml) and 3A molecular sieves (activated at 190° C. for 18 hours in vacuum). After stirring for 1 hour under a CaCl$_2$ drying tube, sodium cyanoborohydride (2.0 g, 31.9 mmol) was added in small portions over 2 minutes. After an additional 3 hours of stirring the reaction was filtered and the sieves were washed with methanol. The methanol was spin evaporated in vacuo to give a residual foam. This foam was added to a column (40 mm×180 mm) of silica Gel 60 wetted with ethyl acetate and eluted using the "flash chromatography technique" (W. C. Still, M. Kahn, and A. Mitra, *J. Org. Chem.* 43, 2923, 1978). The column was washed with 1 litre of ethyl acetate followed by methanol/dichloromethane (1:9) to elute the product. The fractions containing product were combined and spin evaporated in vacuo to yield 8.2 g of the acetylated ester intermediate, mp 175°–180° C. A solution of 7.2 g of this intermediate was dissolved in aqueous sodium hydroxide (1N, 500 ml) and ethanol (250 ml) and stirred at 55° C. for 18 hours. The reaction solution was concentrated to 100 ml by spin evaporation in vacuo. The pH was adjusted to 4.0 with concentrated hydrochloric acid (12N). After cooling, the precipitate was collected and washed with water and ether. The product was sucked dry to give 6.0 g (52%) of crude product that was recrystallized by dissolution in 2-methoxyethanol (75 ml), filtration and slow addition to ethanol (200 ml) was stirring to give 1.02 g of N-[4-[3-(2,4-diamino-1,6-dihydro-6-oxo-5-pyrimidinyl]propylamino]benzoyl-L-glutamic acid, mp 195°–200°, which was identical to that prepared via the compound of formula (V).

EXAMPLE 2

Preparation of N-[4-[3-(2,4-diamino-1,6-dihydro-6-dihydro-6-oxo-5-pyrimidinyl)-N-methylpropylamino]benzoyl]-L-glutamic acid To a stirred solution of 1.99 g (3.6 mmol) of dimethyl N-[4-[3-(2,4-bis(acetamido)-1,6-dihydro-6-oxo-5-pyrimidinyl)propylamino]benzoyl]-L-glutamate in 50 ml of acetonitrile and 5 ml of dimethylformamide was added 2 ml of 37% aqueous formaldehyde followed by 0.50 g (8.0 mmol) of sodium cyanoborohydride and 2 ml of acetic acid. After 18 hours the mixture was filtered to remove the solids and the filtrate was spin evaporated in vacuo. The residue was diluted with 100 ml of ice water, and then extracted with four 25 ml portions of methylene dichloride. The combined extracts were filtered through glass wool and spin evaporated in vacuo to give 2.1 g of the title compound as an oil which was a single spot on TLC. The oil was dissolved in 50 ml of ethanol and 50 ml of 1N sodium hydroxide and stirred at 70° C. for 20 hours. The reaction was cooled and spin evaporated in vacuo to a syrup. The syrup was dissolved in 50 ml of water, cooled on ice, and acidified to pH 3–4 with concentrated hydrochloric acid. The white solids were collected, washed with water, and finally with ether; yield, 1.10 g (67%), mp 190°–200° C. (one spot on TLC). Recrystallization from ethanol gave the analytical sample; yield, 0.54 g (33%, mp (166°–1678° changes to hard foam) 198°–204°; TLC (pyridine:BuOH:H$_2$O/1:1:1); NMR (DMSO-d$_6$)δ8.16 (d, 1H, ArCONH), 7.71 (d, 2H, Ar), 6.66 (d, 2H, Ar), 5.94 (s, 2H, NH$_2$), 5.76 (s, 2H, NH$_2$) 4.36 (m, 1H, CHCO$_2$H), 3.34 (m, 2H, CH$_2$N(CH$_3$)Ar), 2.93 (s, 3H, NCH$_3$).

Elemental analysis: Calculated for C$_{20}$H$_{26}$N$_6$O$_6$·½H$_2$O: C, 52.7; H, 5.98; N, 18.4. Found: C, 52.6; H, 5.95; N, 18.4.

EXAMPLE 3

Preparation of
N-[4-[3-(2,4-Diamino-1,6-dihydro-6-oxo-5-pyrimidinyl)-N-formylpropylamino]benzoyl]-L-glutamic acid A solution of 1.16 g (2.5 mmol) of N-[4-[3-(2,4-diamino-1,6-dihydro-6-oxo-5-pyrimidinyl)-propylamino]benzoyl]-L-glutamic acid in the solution prepared from 25 ml of 97% formic acid and 5 ml of acetic anhydride was heated on an oil bath at reflux for 1 hour. The reaction was cooled and spin evaporated in vacuo to give a hard foam, which was repeatedly covered with ethanol and reevaporated. The foam was triturated under ethanol with a magnetic stirring bar overnight to give a fine solid which was collected, washed with ethanol, and sucked dry; yield, 1.22 g (98%), mp 130°–160° (eff). Several recrystallizations from ethanol gave analytically pure material; yield, 0.496 g (40%), mp 170°–180° C. (eff); NMR (DMSO-$d_6$)$\delta$8.63 (d, 1H, ArCON$\underline{H}$), 8.53 and 8.37 (two s in ratio 9 to 1 at 29° C., coalesce to a singlet at 120° C., 1H, $\underline{H}$CON), 7.93 (d, 2H, ArH), 7.56 (s, ArH of one formanilide isomer), 7.44 (d, 2H, ArH), 5.93 and 5.70 (two s, 4H, two NH$_2$), 4.41 (m, 1H, C$\underline{H}$CO$_2$H), 3.78 (m, 2H, C$\underline{H_2}$N (CHO)Ar).

Elemental analysis: Calculated for $C_{20}H_{24}N_6O_7$, $H_2O$: C, 50.2; H, 5.48; N, 17.6. Found: C, 50.2; H, 5.16; N, 17.9.

EXAMPLE 4

Preparation of
N-[4-[2-(2,4-diamino-1,6-dihydro-6-oxo-5-pyrimidinyl)ethylamino]benzoyl]-L-glutamic acid (a) Preparation of 1-(2-acetamido-4-diacetylamino-1,6-dihydro-6-oxo-5-pyrimidinyl)acetaldehyde diethyl acetal Freshly distilled acetic anhydride (250 ml) was added to a solution of 2-(2,4-diamino-1,6-dihydro-6-oxo-5-pyrimidinyl)acetaldehyde diethyl acetal (*Chem. Ber.*, 1977, 110, 1462) (50.0 g, 0.206 mol). The solution was protected from moisture and heated on a steam bath with magnetic stirring for 5 days. The reaction was spin evaporated in vacuo with the addition of ethylene glycol monomethyl either under aspirator and finally mechanical pump vacuum. The residue was recrystallized from ether to yield 23.0 g (30% of theory) of 2-(2-acetylamino-4-diacetylamino-1,6-dihydro-6-oxo-5-pyrimidinyl)acetaldehyde diethyl acetal, mp 128°–130°. The analytical sample was prepared by dissolving the sample in chloroform and washing the solution through Superfiltrol $\mu$19 (Filtrol Corporation). The solution was spin evaporated in vacuo and the residue was recrystallized from ether/cyclohexanes, to give analytically pure material, mp 129°–130°.

Elemental analysis: Calculated for $C_{16}H_{24}N_4O_6$ (MW 368.40): C, 52.17; H, 6.97; N, 15.20. Found: C, 51.82; H, 6.50; N, 15.25.

(b) Preparation of 2-(2-acetylamino-4-diacetylamino-1,6-dihydro-6-oxo-5-pyrimidinyl)acetaldehyde Method 1: A slurry of Silica Gel 60 (6.0 g, Merck $\mu$7734, 70–230 mesh) and aqueous oxalic acid (10%) (0.6 ml) in dichlormethane (12 ml) was stirred for 15 minutes. 2-(2-acetylamino-4-diacetylamino-1,6-dihydro-6-oxo-5-pyrimidinyl)acetaldehyde diethyl acetate (1.0 g, 2.7 mmol) was added and the mxiture was stirred for 18 hours. Sodium bicarbonate (0.2 g, 2.4 mmol) was added and after 10 minutes the slurry was filtered and washed with ethyl acetate. The filtrates and wash were combined and spin evaporated in vacuo to give 0.37 g (46% of theory) of 2-(2-acetylamino-4-diacetylamino-1,6-dihydro-6-oxo-5-pyrimidinyl)acetaldehyde. The analytical sample was prepared by recrystallization from acetone to give 0.21 g (26% of theory), mp 169°–170° C.)

Elemental analysis: Calculated for $C_{12}H_{14}N_4O_5$ (MW 294.27): C, 48.98; H, 4.80; N, 17.08. Found: C, 48.90; H, 4.83; N, 19.26

Method 2: A solution 2-(2-acetylamino-4-diacetylamino-1,6-dihydro-6-oxo-5-pyrimidinyl)acetaldehyde diethyl acetal (2.0 g, 5.4 mmol) and 4-toluenesulfonic acid monohydrate (0.050 g, 0.26 mmol) in acetone (100 ml) was stirred for 2 days. The solids were collected, washed with acetone and dried to give 0.73 g (46% of theory) of 2-(2-acetylaminor-4-diacetylamino-1,6-dihydro-6-oxo-5-pyrimidinyl)acetaldehyde, mp 168°–170° which was identical to that prepared by method 1.

(c) Preparation of dimethyl N-[4-[2-(2-acetylamino-4-diacetylamino-1,6-dihydro-6-oxo-5-pyrimidinyl)ethylamino]benzoyl]-L-glutamate hydrate A solution of 2-(2-acetylamino-4-diacetylamino-1,6-dihydro-6-oxo-5-pyrimidinyl)acetaldehyde (1.74 g, 5.92 mmol) and dimethyl N-(4-aminobenzoyl)-L-glutamate (*J. Am. Chem. Soc.*, 1958, 80, 5779) (1.74 g, 5.92 mmol) in acetic acid (90 ml) was stirred for 10 minutes. Sodium cyanoborohydride (0.84 g, 13.4 mmol) was added in small portions over 1 hour. After an additional 30 minutes, the reaction was spin evaporated in vacuo to a thick oil. The oil was dissolved in ethyl acetate (500 ml) and washed with 5% aqueous sodium bicarbonate until neutral, water (50 ml), brine (50 ml), dried with magnesium sulfate and spin evaporated in vacuo. Recrystallization from ethyl acetate, with filtration to remove insolubles, yielded 1.5 g (49% of theory) of dimethyl N-[4-[2-(2-acetylamino-4-diacetylamino-1,6-dihydro-6-oxo-5-pyrimidinyl)ethylamino]benzoyl]-L-glutamate, mp 168°–178° C. Recrystallization from ethyl acetate (Norite) gave 0.830 g (25% of theory) of the analytical sample, mp 176°–179° C.

Elemental analysis: Calculated for $C_{26}H_{32}N_6O_9 \cdot H_2O$ (MW 590.60: C, 49.79; H, 5.68: N, 18.93. Found: C, 49.62; H, 5.53; N, 18.87.

(d) Preparation of N-[4-[2-(2,4-diamino-1,6-dihydro-6-oxo-5-pyrimidinyl)ethylamino]benzol]-L-glutamic acid A crude preparation of dimethyl N-[4-[2-(2-acetylamino-4-diacetylamino-1,6-dihydro-6-oxo-5-pyrimidinyl)ethylamino]benzoyl]-L-glutamate hydrate (prepared on a 3.3 mmol scale but without recrystallization) was dissolved in 1N sodium hydroxide (100 ml) and ethanol (50 ml) containing 2-mercaptoethanol (0.25 ml). The reaction was heated with stirring to 55° for 18 hours and then spin evaporated in vacuo to a small volume. The pH of the ice bath cooled solution was adjusted to pH 4 with hydrochloric acid (12 N) to precipiate the product. Recrystallization from methanol/ether gave 0.52 g (38% of theory) of N-[4-[2-(2,4-diamino-1,6-dihydro-6-oxo-5-pyrimidinyl)ethylamino]benzoyl]-L-glutamic acid, mp 180°–185°.

Elemental analysis: Calculated for $C_{18}H_{22}N_6O_6 \cdot H_2O$ 0.1 Et$_2$O (MW 443.84): C 49.79; H, 5.68; N, 18.92. Found: C, 49.62; H, 5.53; N, 18.87.

EXAMPLE 5

Preparation of
N-[4-[2-(2,4-diamino-1,6-dihydro-6-oxo-5-pyrimidinyl)ethyl-N-methylamino]benzoyl]-L-glutamic acid (a) Preparation of dimethyl N-[4-[2-(2,4-bis-(acetamido)-1,6-dihydro-6-oxo-5-pyrimidinyl)ethyl-N-methylamino]benzoyl]-L-glutamate.

A solution of 2-(2-acetylamino-4-diacetylamino-1,6-dihydro-6-oxo-5-pyrimidinyl)acetaldehyde (2.93 g, 10 mmol) and dimethyl N-(4-aminobenzoyl)-L-glutamate (2.93 g, 10 mmol) in acetic acid (200 ml) was stirred at ambient temperature for 15 minutes. Sodium cyanoborohydride (0.350 g, 5.6 mmol) was added, and after an additional 10 minutes aqueous formaldehyde (37%) (4.2 ml) was added. After 10 minutes additional sodium cyanoborohydride (1.5 g, 23.9 mmol) was added and the reaction was stirred for 3 minutes. The solvent was removed by spin evaporation in vacuo at 50° C. The viscous oil was dissolved in chloroform:methanol (1:10, 500 ml) and extracted with water (50 ml), 5% aqueous sodium bicarbonate (10 ml) and dried over magnesium sulfate. After spin evaporation in vacuo the residue was recrystallized from ether to give 3.14 g of a pale yellow powder. The product was purified by open column chromatography on a Silica Gel 60 (Merck $\mu$7734, 63–200 $\mu$M) column (3 cm × 25 cm column) wetted with dichloromethane and eluted with 4% methanol in dichloromethane. The appropriate fractions were combined and spin evaporated in vacuo, and the residue was recrystallized from ethyl acetate to yield 1.3 g (22% of theory) of dimethyl N-[4-[2-(2,4-bis(acetamido)-1,6-dihydro-6-oxo-5-pyrimidinyl)ethyl-N-methylamino]benzoyl]-L-glutamate, mp 168°–175°.

Elemental analysis: Calculated for $C_{25}H_{33}N_6O_8 \cdot 0.5 H_2O$ (MW 5534.58): C, 54.24: H, 6.01; N, 15.18. Found: C, 53.88; H, 5.75, N, 15.28.

(b) Preparation of N-[4-[2-(2,4-diamino-1,6-dihydro-6-oxo-5-pyrimidinyl)ethyl-N-methylamino]benzoyl]-L-glutamic acid A solution of dimethyl N-[4-[2-(2-acetylamino-4-diacetylamino-1,6-dihydro-6-oxo-5-pyrimidinyl)ethyl-N-methylamino]benzoyl]-L-glutamate (0.25 g, 0.43 mmol), 2-mercaptoethanol (0.25 ml), 1N sodium hydroxide (20 ml) and ethanol (10 ml) was stirred under nitrogen for 18 hours at 60° C. The reaction was cooled in an ice bath, and the pH of the solution was adjusted to 4 with hydrochloric acid (12 N). The resultant precipitate was collected and recrystallized from ethanol containing 2-mercaptoethanol (0.25 ml) to yield 0.077 g (41% of theory) of N-[4-[2-(2,4-diamino-1,6-dihydro-6-oxo-pyrimidinyl)ethyl-N-methylamino]benzoyl]-L-glutamic acid, m.p. 180°–188°. This material was a white powder which became tan upon extended exposure to light.

Elemental analysis: Calculated for $C_{19}H_{24}N_6O_6 \cdot H_2O$ (MW 450.46): C, 50.66; H, 5.82; N, 18.66. Found: C, 50.49; H, 5.77; 18.52.

EXAMPLE 6

Preparation of
N-[4-[3-(2,4-diamino-1,6-dihydro-6-oxo-5-pyrimidinyl)-propylamino]benzoyl]-L-glutamyl-L-glutamic acid (2)
and
N-[4-[3-(2,4-diamino-1,6-dihydro-6-oxo-5-pyrimidinyl)-propylamino]benzoyl]-L-glutamyl-L-glutamyl-L-glutamic acid (3)

Compounds 2 and 3 were enzymatically synthesized from N-[4[3-(2,4-diamino-1,6-dihydro-6-oxo-5-pyrimidinyl)propylamino]benzoyl]-L-glutamic acid (1) hydrate, and L-glutamic acid by *E. coli* folylpoly-Y-glutamate synthetase (Bognar), A .S., Osborn,C., Shane, B., Singer, S. C., and Ferone, R. *J. Biol. Chem.* 260, 5625–5630 (1985)). The 20 hr reaction was done in an amber, gas-tight bottle in a gently shaking 37° C. $H_2O$ bath. The argon-saturated 200 ml reaction contained 4 $\mu$moles $^{14}$C-(1) labeled in the benzoyl carbonyl, 40 $\mu$moles L-glutamic acid, 1 mmol KCl, 4 mg bovine serum albumin, 1.4 mmoles 2-mercaptoethanol (2-MET), 0.1 mmole adenosine-5'-triphosphate, 0.2 mmole $MgCl_2$, 2 mmole Tris.HCl ph 8.6 (37°) and 50 units of enzyme. HPLC analysis of 100 $\mu$l of the reaction mixture after 20 hr revealed two $^{14}$C-containing products and no remaining $^{14}$C-(1).

The reaction mixture was adjusted to pH 1 with 2.8 ml of 10% wt/vol trifluoroacetic acid (TFA). It was protected from light during all handling. A 5.0 ml portion was desalted on a Waters $C_{18}$ Sep-Pak which had been prewashed with 5 ml 2-propanol (ISP), 10 ml $H_2O$ and 5 ml 0.1% wt/vol TFA. The $^{14}$C-containing products were retained on the Sep-Pak during a 10 ml 0.1% wt/vol TFA wash and eluted with 8 ml 0.1% TFA, 50% ISP into 50 $\mu$l 2-MET. The eluant was argon saturated in a sealed amber bottled, shell-frozen and lyophilized. The dried sample was dissolved in 1.0 ml 3% acetonitrile (ACN) in HPLC solvent (0.14 M sodium acetate pH 6.4, 0.05% triethylamine) and passed through a 0.45 $\mu$m Millipore HV filter. The filtrate (840 $\mu$l) was chromatographed on a 10 cm Waters $C_{18}$ Nova-Pak Radial Compression Column at 1 ml/min (1.5% ACN in HPLC solvent for 15 minutes followed by 2.4% ACN in HPLC solvent). Two $^{14}$C-containing peaks, identified as (3) and (2) were eluted at 27 and 33 minutes, respectively. Samples were adjusted to pH 1, desalted on $C_{18}$ Sep-Paks, eluted into 2-Met, argon-saturated and freeze-dried as above. Dried samples were each dissolved in 0.5 ml of argon-saturated 500 $\mu$M NaOH. Final yield was 191 nmoles (3) and 337 nmoles (2). The sum equals 71% overall yield from (1).

The identities of (3) and (2) were established by hydrophobic chromatography of the intact molecules and of their $KMnO_4$-$H_2O_2$ induced cleavage products. It is known that the oxidation state of pteroylpolyglutamates and close analogues is the primary factor in their retention on $C_{18}$ at pH 2. Such compounds, with 1 to 7 glutamates, are retained in 0.1% TFA, 4% ACN and elute in a single sharp peak after 684 seconds in 1 ml/min 0.1% TFA, 12% ACN. Compounds (3) and (2) co-chromatographed with (1) under the above conditions. This showed that the pyrimidinylpropyl moiety of the compounds was the same as in the parent (1).

The glutamate chain length of (3) and (2) was established after cleavage of the compounds at the propylamino C-N bond. (A 1.0 ml solution at pH 9 was oxidized with 100 $\mu$l 2% $KMnO_4$. After one minute, 80

μl 30% H₂O₂ was added the precipitate KMnO₂. Excess H₂O₂ was destroyed by the addition of 20 μl of 11 μg/ml beef liver catalase (Worthington Biochemical Corp.). The $^{14}$C-labeled oxidation products of (3) and (2) co-chromatographed (on C$_{18}$ in 0.1% TFA, 4% ACN), respectively, with 4-aminobenzoyl-L-glutamyl-L-glutamyl-L-glutamic acid (PABG$_3$) and 4-aminobenzyl-L-glutamyl-L-glutamic acid (PABG$_2$). This shows that the compound assigned as (3) contains three glutamic acid residues attached to 4-aminobenzoic acid. The compound assigned as (2) contains two glutamic acid residues attached to 4-aminobenzoic acid. As in the PABG$_2$ and PABG$_3$ standards, the peptide linkages are through the α-carboxyls of the glutamates.

EXAMPLE 7

Preparation of N-[4-[N-[3-(2,4-diamino-1,6-dihydro-6-oxo-5-pyrimidinyl)propyl]amino]benzoyl]-L-gamma-glutamyl-L-gamma-glutamyl-L-gamma-glutamyl-L-gamma-glutamyl-L-gamma-glutamyl-L-glutamic acid (a) Preparation of N-(Benzyloxycarbonyl)-L-gamma-glutamyl-L-glutamic acid tris(tert-butyl)ester To a stirred solution of 3.89 g (7.5 mmol) of N-(benzyloxycarbonyl)-L-glutamic acid alpha-(tert-butyl)ester dicyclohexylamine salt, 2.22 g (7.5 mmol) of L-glutamic acid bis(tert-butyl)ester hydrochloride, and 1.01 g (7.5 mmol) of 1-hydroxybenzotriazole in 20 ml of dichloromethane was added 1.70 g (8.25 mmol) of 1,3-dicyclohexylcarbodiimide. The reaction was stirred for 17 hours and filtered. The filtrate was sequentially washed with saturated aqueous sodium bicarbonate (2×40 ml), dried with magnesium sulfate, filtered, and spin evaporated in vacuo. The product was purified by flash chromatography on silica gel 60 (150 g, 230–400 mesh, EM Reagents) with hexanes: ethyl acetate (1:1). The appropriate fractions were combined on the basis of TLC correlation and spin evaporated in vacuo to yield 3.34 g (77% of theory) of N-(benzyloxycarbonyl)-L-gamma-glutamyl-L-glutamic acid tris(tert-butyl)ester as a colorless gum: TLC (hexanes:ethyl acetate-3:1), R$_f$=0.4 (anisaldehyde); NMR (DMSO-d$_6$) δ 1.39 (s, 27H, O-t-Bu), 1.70 (m, 2H, α-CH$_2$), 1.85 (m, 2H, α-CH$_2$), 2.20 (m, 4H, β-CH$_2$, 4.00 (m, 2H, α-H), 5.04 (s, 2H, NCO$_2$CH$_2$), 7.35 (s, 5H, Ar), 7.55 (d, 1H, NH), 8.05 (d, 1H, NH).

Elemental analysis: Calculated for C$_{30}$H$_{46}$N$_2$O$_9$ (MW 578.70): C, 62.27: H, 8.01; N, 4.84. Found: C, 61.99; H, 8.03; NH, 4.79.

(b) Preparation of L-gamma-Glutamyl-L-glutamic acid tris(tert-butyl)ester

A solution of 3.34 g (5.77 mmol) of N-(benzyloxycarbonyl)-L-gamma-glutamyl-L-glutamic acid tris(tert-butyl)ester in 100 ml of 95% ethanol and 80 mg of 10% palladium on carbon was shaken in the presence of hydrogen at 22 psi of hydrogen for 18 hours. The catalyst was removed by filtration and the filtrate was spin evaporated in vacuo to yield 2.39 g (93% of theory) of L-gamma-glutamyl-L-glutamic acid tris(tert-butyl)ester as a colorless syrup; TLC (ethyl acetate), R$_f$=0.3 (ninhydrin). The product was used in the next reaction without further characterization.

(c) Preparation of N-(Benzyloxycarbonyl)-L-gamma-glutamyl-L-gamma-glutamyl-L-glutamic acid tetrakis(tert-butyl)ester To a stirred mixture of 2.79 g (5.38 mmol) of N-(benzyloxycarbonyl)-L-glutamic acid alpha-(tert-butyl)ester dicyclohexylamine salt, 2.39 g (5.38 mmol) of L-gamma-glutamyl-L-glutamic acid tris(tert-butyl)ester, 0.73 g (5.38 mmol) of 1-hydroxybenzotriazole and 5.38 ml of 1.0 N hydrochloric acid in 30 ml of dichloromethane was added 1.22 g (5.91 mmol) of 1,3-dicyclohexylcarbodiimide. The reaction was stirred for 16 hours and filtered. The filtrate was sequentially washed with saturated aqueous sodium bicarbonate (2×50 ml), 5% aqueous citric acid (2×50 ml) and saturated brine (2×50 ml), dried with magnesium sulfate, filtered, and spin evaporated in vacuo. The product was purified by flash chromatography on Silica Gel 60 (150 g, 230–400 mesh, EM Reagents) with ethyl acetate:hexanes (1:1). The appropriate fractions were combined on the basis of TLC correlation and spin evaporated in vacuo to yield 3.10 g (75% of theory) of N-(benzyloxycarbonyl)-L-gamma-glutamyl-L-gamma-glutamyl-L-glutamic acid tetrakis(tert-butyl)ester, mp 76°–78°: TLC (hexanes:ethyl acetate-1:1), R$_f$=0.4 (anisaldehyde); NMR (DMSO-d$_6$) δ 1.39 (s, 36H, O-tBu), 1.75 (m, 3H, α-CH$_2$), 2.22 (m, 6H, β-CH$_2$), 3.90 (m, 1H, α-H), 4.10 (m, 2H, α-H), 5.04 (dd, 2H, NCO$_2$CH$_2$), 7.36 (s, 5H, Ar), 7.61 (d, 1H, NH), 8.09 (m, 2H, NH).

Elemental analysis. Calculated for C$_{39}$H$_{61}$N$_3$O$_{12}$ (MW 763.92): C, 61.32; H, 8.05; N, 5.50. Found: C, 61.09: H, 8.21; N, 5.45.

(d) Preparation of L-gamma-glutamyl-L-gamma-glutamyl-L-glutamic acid tetrakis(tert-butyl)ester A solution of 3.10 g (4.06 mmol) of N-(benzyloxycarbonyl)-L-gamma-glutamyl-L-gamma-glutamyl-L-glutamic acid tetrakis(tert-butyl)ester in 100 ml of 95% ethanol and 100 mg of 10% palladium on carbon was shaken in the presence of hydrogen at 22 psi for 8 hours. The catalyst was removed by filtration and the filtrate was spin evaporated in vacuo to yield 2.23 g (87% of theory) of L-gamma-glutamyl-L-gamma-glutamyl-L-glutamic acid tetrakis(tert-butyl)ester as a colorless gum; TLC (95% ethanol), R$_f$=0.7 (ninhydrin). The product was used in the next reaction without other characterization.

(e) Preparation of N-(Benzyloxycarbonyl)-L-gamma-glutamyl-L-gamma-glutamyl-L-gamma-glutamyl-L-glutamic acid pentakis(tert-butyl)ester To a stirred mixture of 1.83 g (3.52 mmol) of N-(benzyloxycarbonyl)-L-glutamic acid alpha-(tert-butyl)ester dicyclohexylamine salt, 2.23 g (3.52 mmol) of L-gamma-glutamyl-L-gamma-glutamyl-L-glutamic acid tetrakis(tert-butyl)ester, 0.474 g (3.52 mmol) of 1-hydroxybenzotriazole and 3.52 ml of 1.0 N hydrochloric acid in 25 ml of dichloromethane was added 0.800 g (3.88 mmol) of 1,3-dicyclohexylcarbodiimide. The reaction was stirred for 17 hours and filtered. The filtrate was sequentially washed with saturated aqueous sodium bicarbonate (2×50 ml), 5% aqueous citric acid n2×50 ml) and saturated brine (2×50 ml), dried with magnesium sulfate, filtered, and spin evaporated in vacuo. The product was purified by flash chromatography on Silica Gel 60 (150 g, 230–400 mesh, EM Reagents), with hexanes:ethyl acetate (3:7). The appropriate fractions were combined on the basis of TLC correlation and spin evaporated in vacuo to yield 2.71 g (81% of theory) of N-(benzyloxycarbonyl)-L-gamma-glutamyl-L-gamma-glutamyl-L-gamma-glutamyl-L-glutamic acid pentakis(tert-butyl)ester, mp 75°; TLC (hexanes:ethyl acetate-3:7), R$_f$=0.5 (anisaldehyde); NMR (DMSO-d$_6$) δ 1.39 (s, 45H, O-tBu), 1.75 (m, 4H, α-CH$_2$), 1.92 (m, 4H, α-CH$_2$), 1.92 (m, 4H, α-CH$_2$), 2.22 (m, 8H, β-CH$_2$), 3.89 (m, 1H, α-H), 4.10 (m, 3H, α-H), 5.04 (dd, 2H, NCO$_2$CH$_2$), 7.37 (s, 5H, Ar), 7.63 (d, 1H, NH), 8.0 (m, 3H, NH).

Elemental analysis. Calculated for $C_{48}H_{76}N_4O_{15}$ (MW 949.115): C, 60.74; H, 8.07; N, 5.90. Found C, 60.91; H, 8.09; N, 6.11.

(f) Preparation of L-gamma-glutamyl-L-gamma-glutamyl-L-gamma-glutamyl-L-glutamic acid pentakis(tert-butyl)ester A solution of 2.71 g (2.86 mmol) of N-(benzyloxycarbonyl)-L-gamma-glutamyl-L-gamma-glutamyl-L-gamma-glutamyl-L-glutamic acid pentakis(tert-butyl)ester in 100 ml of 95% ethanol and 100 mg of 10% palladium on carbon was shaken in the present of hydrogen at 40 psi for 19 hours. The catalyst was removed by filtration and the filtrate was spin evaporated in vacuo to yield 2.29 g (98% of theory) of L-gamma-glutamyl-L-gamma-glutamyl-L-gamma-glutamyl-L-glutamic acid pentakis(tert-butyl)ester as a white foam; TLC (ethyl acetate:methanol -9:1), $R_f$=0.5 (ninhydrin). The product was used in the next reaction without further characterization.

(g) Preparation of N-(Benzyloxycarbonyl)-L-gamma-glutamyl-L-gamma-glutamyl-L-gamma-glutamyl-L-gamma-glutamyl-L-glutamic acid hexakis(tert-butyl)ester To a stirred mixture of 1.46 g (2.80 mmol) of N-(benzyloxycarbonyl)-L-glutamic acid alpha-(tert-butyl)ester dicyclohexylamine salt, 2.29 g (2.80 mmol) of L-gamma-glutamyl-L-gamma-glutamyl-L-gamma-glutamyl-L-glutamic acid pentakis(tert-butyl)ester, 0.380 g (2.80 mmol) of 1-hydroxybenzotriazole and 2.8 ml of 1.0 N hydrochloric acid in 35 ml of dichloromethane was added 0.635 g (3.08 mmol) of 1,3-dicyclohexylcarbodiimide. The reaction was stirred for 19 hours and filtered. The filtrate was sequentially washed with saturated aqueous sodium bicarbonate (2×25 ml), dried with magnesium sulfate, filtered, and spin evaporated in vacuo. The product was purified by flash chromatography on Silica Gel 60 (150 g, 230–400 mesh, EM Reagents) with hexane:ethyl acetate (1:2). The appropriate fractions were combined on the basis of TLC correlation and spin evaporated in vacuo to yield 2.40 g (76% of theory) of N-(benzyloxycarbonyl)-L-gamma-glutamyl-L-gamma-glutamyl-L-gamma-glutamyl-L-gamma-glutamyl-L-glutamic acid hexakis(tert-butyl)ester as a white foam, mp 74°–76°; TLC (hexanes:ethyl acetate-1:2), $R_f$=0.4 (anisaldehyde).

Elemental analysis. Calculated for $C_{57}H_{91}H_5O_{18}$ (MW 1134.37): C, 60.35: H, 8.09; N, 6.17. Found: C, 59.94; H, 8.16; N, 5.89.

(h) Preparation of L-gamma-glutamyl-L-gamma-glutamyl-L-gamma-glutamyl-L-gamma-glutamyl-L-glutamic acid hexakis(tert-butyl)ester A solution of 2.40 g (2.11 mmol) of N-(benzyloxycarbonyl)-L-gamma-glutamyl-L-gamma--glutamyl-L-gamma--glutamyl-L-glutamic acid hexakis(tert-butyl)ester in 100 ml of 95% ethanol and 200 mg of 10% palladium on carbon was shaken in the presence of hydrogen at 45 psi for 4.5 hours. The catalyst was removed by filtration. The filtrate was spin evaporated in vacuo to yield 2.14 g (100% of theory of L-gamma-glutamyl-L-gamma-glutamyl-L-gamma-glutamyl-Lgamma-glutamyl-L-glutamic acid hexakis(tert-butyl)ester as colorless gum; TLC (ethyl acetate:methanol-9:1), $R_f$—0.3 (ninhydrin). The product was used in the next reaction without further characterization.

(i) Preparation of N-(Benzyloxycarbonyl)-L-gamma-glutamyl-L-gamma--glutamyl-L-gamma--glutamyl-L-gamma-glutamyl-L-gamma-glutamic acid heptakis(tert-butyl)ester To a stirred mixture of 1.11 g (2.14 mmol) of N-(benzyloxycarbonyl)-L-glutamic acid alpha-(tert-butyl)ester dicyclohexylamine salt, 2.14 g (2.14 mmol) of L-gamma-glutamyl-L-gamma-glutamyl-L-gamma-glutamyl-L-gamma-glutamyl-L-glutamic acid hexakis(tert-butyl)ester, 0.289 g (2.14 mmol) of 1-hydroxybenzotriazole and 2.14 ml of 1.0 N hydrochloric acid in 20 ml of dichloromethane was added 0.486 g (2.35 mmol) of 1,3-dicyclohexylcarbodiimide. The reaction was stirred for 18 hours and filtered. The filtrate was sequentially washed with saturated aqueous sodium bicarbonate (2×50 ml), 5% aqueous citric acid (2×50 ml) and saturated brine (2×25 ml), dried with magnesium sulfate, filtered, and spin evaporated in vacuo. The product was purified by flash chromatography on Silica Gel 60 (150 g, 230–400 mesh, EM Reagents) with hexanes:ethyl acetate (1:3). The appropriate fractions were combined on the basis of TLC correlation and spin evaporated in vacuo to yield 2.03 g (72% of theory) of N-(benzyloxycarbonyl)-L-gamma-glutamyl-L-gamma-glutamyl-L-gamma-glutamyl-L-gamma-glutamyl-L-glutamic acid heptakis(tert-butyl)ester as a white foam, mp 77°–78°; TLC (hexanes:ethyl acetate-1:3), $R_f$=0.4 (anisaldehyde).

Elemental analysis. Calculated for $C_{66}H_{106}N_6O_{21}$ (MW 1319.59): C, 60.07; H, 8.10; N, 6.37. Found: C, 60.00; H, 8.11; N, 6.35.

(j) Preparation of L-gamma-glutamyl-L-gamma-glutamyl-L-gamma-glutamyl-L-gamma-glutamyl-L-gamma-glutamyl-L-glutamic acid heptakis(tert-butyl)ester A solution of 2.00 g (1.52 mmol) of N-(benzyloxycarbonyl)-L-gamma-glutamyl-L-gamma-glutamyl-L-gamma-glutamyl-L-gamma-glutamyl-L-gamma-glutamyl-L-glutamic acid heptakis(tert-butyl)ester in 100 ml of 95% ethanol and 100 mg of 10% palladium on carbon was shaken in the presence of hydrogen at 43 psi for 16 hours. The catalyst was removed by filtration and the filtrate was spin evaporated in vacuo to yield 1.67 g (93% of theory) of L-gamma-glutamyl-L-gamma-glutamyl-L-gamma-glutamyl-L-gamma-glutamyl-L-gamma-glutamyl-L-glutamic acid heptakis(tert-butyl)ester as a white foam, mp 67°–69°; TLC (ethyl acetate:methanol-9:1), $R_f$=0.5 (ninhydrin); NMR (DMSO-d6) δ 1.39 (s, 63H, O-t-Bu), 1.74 (m, 6H, α-$CH_2$), 1.92 (m, 6H, α-$CH_2$), 2.21 (m, 12H, β-$CH_2$), 4.08 (m, 6H, α-H), 8.15 (m, 7H, NH): mass spectrum (chemical ionization) m/z 1186 (85.0% relative abundance; (M+H+), m/z 1001 (27.5%), m/z 815 (100%).

Elemental analysis. Calculated for $C_{58}H_{100}N_6O_{19}$ (MW 1185.46): C, 58.77; H, 8.50; N, 7.09. Found: C, 58.78; H, 8.58; N, 7.03.

(k) Preparation of Ethyl 4-[3-[2-(Acetylamino)-4-(diacetylamino)-1,6-dihydro-6-oxo-5-pyrimidinyl]-propylamino]benzoate A mixture of 1.25 g (4.00 mmol) of 3-[2-(acetylamino)-4-(diacetylamino)-1,6-dihydro-6-oxo-5-pyrimidinyl]propionaldehyde, 0.743 g (4.50 mmol) of ethyl p-aminobenzoate, 1.0 ml of glacial acetic acid, and 3A molecular sieves in 25 ml of methanol was stirred at room temperature for 3 hours under nitrogen before 0.28 g (4.47 mmol) of sodium cyanoborohydride was added during a 2 minute period. After stirring for 17 hours, the mixture was filtered. The filtrate was spin evaporated in vacuo to a yellow foam. The product was separated from a mixture by flash chromatography on Silica Gel 60 (100 g; 230–400 mesh, EM Reagents) with ethyl acetate. Appropriate fractions were combined on the basis of TLC correlation, and solent was removed by spin evaporation in vacuo. Recrystallization from ethyl acetate yielded 0.44 g (24% of theory) of ethyl 4-[3-[2-(acetylamino)-4-(diacetylamino)-1,6-dihydro-6-oxo-5-pyrimidinyl]propylamino]benzoate as a white solid, mp 197°–198°; TLC (ethyl acetate), $R_f=0.5$; NMR (DMSO-$d_6$) δ 1.28 (t, J=7.1 Hz, 3H, $CH_3$), 1.65 (m, 2H, $CCH_2C$), 2.14 (s, 3H, Ac), 2.2 (m, 2H, $CH_2$Het), 2.23 (s, 6H, 2Ac), 3.05 (m, 2H, $CH_2N$), 4.22 (q, J=7.1 Hz, 2H, $CO_2CH_2$), 6.5 (br, 1H, AcNH obscured by Ar), 6.57 (d, 2H, ArH), 7.69 (d, 2H, ArH). Elemental analysis. Calculated for $C_{22}H_{27}N_5O_6$, 0.5 $H_2O$ (MW 466.49): C, 56.64; H, 6.05; N, 15.01. Found: C, 56.88; H, 6.01; N, 14.88.

(l) Preparation of 4-[3-(2,4-Diamino-1,6-dihydro-6-oxo-5-pyrimidinyl)propylamino]benzoic acid one-half sodium salt To a solution of 0.22 g (0.47 mmol) of ethyl 4-[3-[2-(acetylamino)-4-(diacetylamino)-1,6-dihydro-6-oxo-5-pyrimidinyl]propylamino]benzoate in 7.0 ml of 95% ethyl alcohol was added 15 ml of 1.0 N NaOH. The reaction was heated at 70° C. for 20 hours. The mixture was reduced by spin evaporation in vacuo to a 10-ml volume and adjusted to pH 5 with 1.0 N HCl. The precipitate was collected by filtration, washed with water, and dried in vacuo to yield 0.11 g (71% of theory) of 4-[3-(2,4-diamino-1,6-dihydro-6-oxo-5-pyrimidinyl)propylamino]benzoic acid one-half sodium salt as a white solid, mp 273°(dec.); HPLC on Versapack C-18 (10 micron; 4.6×250 mm) with aqueous 60% methanol containing 0.2% trifluoroacetic acid gave one major peak, $k^1=0.58$; NMR (DMSO-$d_6$)δ1.58 (m, 2H, $CCH_2C$), 2.24 (t, 2H, Het-$CH_2$), 3.02 (m, 2H, $CH_2N$), 5.77 (br s, 2H, $NH_2$), 5.94 (br s, 2H, $NH_2$), 6.46 (t, 1H, NH-Ar), 6.54 (d, 2H, Ar), 7.65 (d, 2H, Ar), 9.80 (br s, 1H, NH), 11.95 (br s, 0.5 H, $CO_2H$). Elemental analysis. Calculated for $C_{14}H_{16}N_5O_3Na_{0.5}$.0.75 $H_2O$ (MW 327.82); C, 51.29; H, 5.53; N, 21.36; Na, 3.51. Found: C, 51.34; H, 5.39; N, 21.32; Na, 3.33.

(m) Preparation of 4-[N-[3-(2,4-diamino-1,6-dihydro-6-oxo-5-pyrimidinyl)propyl]trifluoroacetamido]benzoic acid A mixture of 0.50 g (1.53 mmol) of 4-[3-(2,4-diamino-1,6-dihydro-6-oxo-5-pyrimidinyl)propylamino]benzoic acid one-half sodium salt 0.75 water and 5.0 ml trifluoroacetic anhydride was stirred at ambient temperature for 18 hours under nitrogen. The amber solution was spin evaporated in vacuo at 25° C. The residual foam was triturated with water (15 ml) until a homogeneous, beige powder was obtained. The solid was collected by filtration, washed with water (2×2 ml) and dried in vacuo to yield 0.617 g (81% of theory) of 4-[N-[3-(2,4-diamino-1,6-dihydro-6-oxo-5-pyrimidinyl)-propyl]trifluoroacetamido]benzoic acid, mp 229°–230°; HPLC on Versapack C-18 (10 micron; 4.6×250 mm) with aqueous 50% methanol containing 0.1% trifluoroacetic acid gave one major peak, $k^1=1.00$; TLC (methanol:ethyl acetate-1:1), $R_f=0.5$; NMR (DMSO-$d_6$) δ 1.50 (m, 2H, $CCH_2C$), 2.20 (t, 2H, Het-$CH_2$), 3.74 (t, 2H, $CH_2N$), 6.67 (br s, 2H, $NH_2$), 7.43 (br s, 2H, $NH_2$), 7.55 (d, 2H, Ar), 8.02 (d, 2H, Ar); mass spectrum (methane chemical ionization) m/z 400 (18.5% relative abundance; [M+H]+), 356 (5.91%, [M−$CO_2$]+), 167 (10.72%), 115 (100%). Elemental analysis. Calculated for $C_{16}H_{16}F_3N_5O_4.CF_3COOH$ (MW 513.353): C, 42.11; H, 3.34; N, 13.64. Found: C, 42.47; H, 3.49; N, 14.13.

(n) Preparation of N-[4-[N-[3-(2,4-Diamino-1,6-dihydro-6-oxo-5-pyrimidinyl) propyl]trifluoroacetamido]-benzoyl]-L-gamma-glutamyl-L-gamma-glutayl-L-gamma-glutamyl-L-gamma-glutamyl-L-gamma-glutamyl-L-glutamic acid heptakis(tert-butyl)ester To 0.10 g (0.20 mmol) of 4-[N-[3-(2,4-diamino-1,6-dihydro-6-oxo-5-pyrimidinyl)propyl]trifluoroacetamido]benzoic acid, 0.24 g (0.20 mmol) of L-gamma-glutamyl-L-gamma-glutamyl-L-gamma--glutamyl-L-gamma-glutamyl-L-gamma-glutamyl-L-glutamic acid heptakis-(tert-butyl)ester, 0.027 g (0.20 mmol) of 1-hydroxybenzotriazole, and 0.020 g (0.20 mmol) of triethylamine in 2.0 ml of N,N-dimethylformamide at ambient temperature was added 0.046 g (0.22 mmol) of 1,3-dicyclohexylcarbodiimide. The reaction was stirred for 22 hours and filtered. The filtrate was spin evaporated in vacuo, and the amber residue was partitioned between dichloromethane (25 ml) and saturated aqueous sodium bicarbonate (15 ml). The organic layer was sequentially washed with saturated sodium bicarbonate (15 ml) and saturated brine (2×10 ml), dried with magnesium sulfate, filtered, and spin evaporated in vacuo to a foam.

The residue was mixed with 5 ml of ethyl acetate; a small amount of insoluble solid was removed by filtration. The filtrate was spin evaporated in vacuo to yield 0.30 g (96% of theory) of N-[4-[N-[3-(2,4-diamino-1,6-dihydro-6-oxo-5-pyrimidinyl)propyl]trifluoroacetamido]benzoyl]-L-gamma-glutamyl-L-gamma -glutamyl-L-gamma-glutamyl-L-gamma-glutamyl-L-gamma-glutamyl-L-glutamic acid heptakis(tert-butyl)ester as a beige solid, mp 114° (dec.); HPLC on Supelco LC-8 with aqueous 80% methanol containing 0.1% triethylamine gave one major peak, $k^1=3.35$; TLC (methanol:ethyl acetate-1:9), $R_f=0.3$ (UV and anisaldehyde); NMR (DMSO-$d_6$)δ1.38 (m, 63H, O-t-Bu), 1.60 (m, 2H, $CCH_2C$), 1.72 (m, 6H, α-$CH_2$), 1.90 (m, 6H, α-$CH_2$), 2.22 (m, 1H, $ArCO_2NHCH$), 5.72 (s, 2H, $NH_2$), 5.90 (s, 2H, $NH_2$), 7.57 (d, 2H, Ar), 7.94 (d, 2H, Ar), 8.13 (m, 6H, α-NH), 9.7 (br, 1H, NH). Elemental analysis. Calculated for $C_{74}H_{114}F_3N_{11}O_{22}$ (MW 1566.77): C, 56.73; H, 7.33; N, 9.83. Found: C, 56.86; H, 7.42; N, 9.79.

(o) Preparation of N-[4-[N-[3-(2,4-diamino-1,6-dihydro-6-oxo-5-pyrimidinyl)propyl]amino]benzoyl]-L-gamma-glutamyl-L-gamma-glutamyl-L-gamma--alutamyl-L-gamma-glutamyl-L-gamma-glutamyl-L-glutamic acid heptakis(tert-butyl)ester To a solution of 0.30 g (0.20 mmol) of N-[4-[N-[3-(2,4-diamino-1,6-dihydro-6-oxo-5-pyrimidinyl)propyl]trifluoroacetamido]benzoyl]-L-gamma-glutamyl-L-gamma-glutamyl-L-gamma-glutamyl-L-gamma-glutamyl-L-gamma-glutamyl-L-glutamic acid heptakis(tert-butyl)ester in 4.0 ml of methanol at ambient temperature was added sequentially 0.045 g (1.0 mmol) of dimethylamine and 0.4 ml of water. Under nitrogen, the yellow solution was stirred at ambient temperature for 18 hours. Reaction progress was monitored by HPLC. The solvent was removed by spin evaporation in vacuo to yield 0.30 g (100% of theory) of N-[4-[N-[3-(2,4-diamino-1,6-dihydro-6-oxo-5-pyrimidinyl)propyl]amino]benozyl-L-gamma-glutamyl-L-gamma-glutamyl-L-gamma-glutamyl-L-gamma-glutamyl-L-gamma-glutamyl-L-glutamic acid heptakis(tert-butyl)ester as a beige solid; HPLC on Supelco LC-8 with aqueous 80% methanol containing 0.1% triethylamine gave one major peak, $k^1=2.44$; TLC (methol:ethyl acetate-1:4), $R_f=0.6$ (UV and anisaldehyde);

NMR (DMSO-d6)δ1.38 (m, 63H, 0-t-Bu), 1.60 (m, 2H, CCH2C), 1.70 (m, 6H, α-CH2), 1.90 (m, 6H, α-CH2), 2.20 (m, 14H, Het-CH2 and β-CH2), 3.00 (m, 2H, CH2), 4.08 (m, 5H, α-H), 4.26 (m, 1H, ArCO2NHCH), 5.75 (s, 2H, NH2), 5.91 (s, 2H, NH2), 6.23 (br, 1H, ArNH), 6.52 (d, 2H, Ar), 7.65 (d, 2H, Ar), 8.14 (m, 6H, β-NH), 9.7 (br, 1H, NH).

(p) Preparation of N-[4-[N-[3(2,4-diamino-1,6-dihydro-6-oxo-5-pyrimidinyl)propyl]amino]benozyl]-L-gamma-glutamyl-L-gamma-glutamyl-L-gamma-glutamyl-L-gamma-glutamyl-L-gamma-glutamyl-L-glutamic acid A mixture of 0.30 g (0.20 mmol) of N-[4-[N-[3-(2,4-diamino-1,6-dihydro-6-oxo-5-pyrimidinyl)propyl]amino]benzoyl]-L-gamma-glutamuyl-L-gamma-glutamyl-L-gamma-glutamyl-L-gamma-glutamyl-L-gamma-glutamyl-L-glutamic acid heptakis(tert-butyl)ester in 5.0 ml of trifluoroacetic acid was stirred at ambient temperature for 0.75 hour. The resulting yellow solution was spin evaporated in vacuo to a beige solid, which was subsequently dissolved in 5.0 ml of water. The aqueous solution was injected into a column of C-18 (comprised of a series of five Rainin Spice cartridges connected in series) preequilibrated with water. The column was washed with 50 ml of water before the product was eluted with 20% acetonitrile. Solvent was removed by spin evaporation and freeze-drying. The residue was partitioned between a 1:1 mixture of ethyl acetate and water. The aqueous layer was freeze-dried to yield 0.12 g (52% of theory) of N-[4-[3-(2,4-diamino-1,6-dihydro-6-oxo-5-pyrimidinyl)propyl]amino]benzoyl]-L-gamma-glutamyl-L-gamma--glutamyl-L-gamma-glutamyl-L-gamma-butamyl-L-gamma-glutamyl-L-glutamic acid as a fluffy white powder, mp 204° (dec.). HPLC on Versapack C-18 (10 micron; 4.6×250 mm) with aqueous 15% acetonitrile containing 0.2% CF3CO2H gave one major peak, $k^1 = 0.77$. 1H NMR (DMSO)δ1.60 (m, 2H, CCH2C), 1.73 (m, 6H, α-CH2N), 1.95 (m, 6H, α-CH2), 2.19 (m, 14H, Het-CH2 and β-CH2), 3.00 (m, 2H, CH2N), 4.13 (m, 5H, α-H), 4.30 (m, 1H, ArCO2NHCH), 5.77 (s, 2H, NH2), 5.95 (s, 2H, NH2), 6.20 (br, 1H, ArNH), 6.53 (d, 2H, Ar), 7.68 (d, 2H, Ar), 8.15 (m, 6H, α-NH), 12.4 (br, COOH signals) plus 0.25 mol EtOAc (1.18 t, 2.00 s, 4.03 q).

Elemental analysis: Calculated for $C_{44}H_{59}N_{11}O_{21} \cdot 2.5 \, H_2O \cdot 0.25 \, EtOAc$ (MW 1145.08): C, 47.20; H, 5.81; N, 13.46. Found: C, 47.35; H, 5.61; N, 13.20.

CHEMOTHERAPEUTIC DATA

A. Anti-neoplastic Activity Data for Lymohocytic Leukemia P388/0 Test

The tests employed for the evaluation of anti-neoplastic activity of the compounds of the present invention are essentially those used in the Tumor Panel of the Developmental Therapeutics Program, Division of Cancer Treatment, National Cancer Institute, A. Goldin, et al., Methods in Cancer Research, Vol. XVI, p. 165, Academic Press (1979). Some modifications, in dose level and schedule have been made to increase the testing efficiency.

CD2-F1-mice, of the same sex, weighing within a 3 g range surrounding 20 g, are used for this test. Control and test animals are injected intraperitoneally with a suspension of $10^6$ viable P388/0 tumor cells on day 0. In each test, several dose levels which bracket the $LD_{20}$ of the compound are evaluated; each dose level group contains six animals. The test compound is prepared either in physiologic saline containing 0.05% Tween 80 or distilled water containing 5% dextrose and is administered intraperitoneally on the indicated schedule relative to tumor implant. Doses are on a mg/kg basis according to individual animals' body weights. The day of death for each animal is recorded, the median identified for each group and the percent increase in life span (% ILS) is calculated from the ratio of survival time of treatment to control groups. The criterion for activity is % ILS greater than or equal to 20%.

The compound of the invention included in this test was the compound of Example 1, namely N-[4-[3-(2,4-diamino-1,6-dihydro-6-oxo-5-pyrimidinyl)-propylamino]benzoyl]-L-glutamic acid and the results are as follows.

| Dose mg/kg | Schedule | % Increased Life Span |
|---|---|---|
| 182 | day 1, 5, 9 | +20 |
| 7.5 | twice a day, on days 1, 2 and 3 | +40 |
| 5 | twice a day, on days 1, 2, and 3 | +35 |
| 2.5 | twice a day, on days 1, 2 and 3 | +20 |
| 5 | every hour for 8 doses on days 1 and 3 | +60 |
| 10 | every 4 hours for 3 doses on days 1–4 | +80 |
| 20 | every hour for 8 doses on days 1 and 3 | +60 |
| 5 | every 4 hours for 3 doses on days 1–4 | +22 |

B. Cell Culture Cytotoxicity Test Data

The two routine indicator cell lines used are (1.) D98, a twice-cloned derivative of Detroit 98s from American Type Culture Collection (ATCC) strain CCL 18.1, from human sternal bone marrow and (2.) L, a cloned derivative from NCTC 929 (ATCC CCL1,) a C3H/An from mouse connective tissue. Inoculation densities for L and D98 cells are 1.0 and $1.5 \times 10^5$ cells, per cm$^2$, respectively. Control cells are grown in Eagle's MEM (Earle's salts, 10% horse serum, 100 units/ml potassium penicillin G and 100 μg/ml streptomycin) and should show at least two doublings during the test period. Test plates are seeded with similar quantities of cells and are grown in the same medium with test compounds added. Total "cell counts" are made with an electronic cell counter after 70–76 hours of incubation with one medium change at 20–26 hours. Dose response curves are prepared by plotting percent of control vs. concentration of compound.

The compounds of the invention included in this test and the results are as follows.

| Compound of Example No. | Concentration ($\times 10^6$ M) | D-98 Cells % of Control | Concentration ($\times 10^6$ M) | L-Cells % of Control |
|---|---|---|---|---|
| 1 | 0.11 | 50 | 0.088 | 50 |
| 2 | 3. | 50 | 0.4 | 50 |
| 3 | 0.21 | 50 | 0.018 | 50 |
| 4 | 0.7 | 50 | 0.4 | 50 |
| 5 | 7 | 50 | 0.75 | 50 |

From the foregoing data, it can, therefore, be concluded that the compounds of the present invention are active in both the lymphocytic leukemia P388/0 and the cell culture cytotoxicity tests and, therefore, that the compounds have anti-neoplastic activity and are able to inhibit neoplastic growth.

C. Reversal of Cytotoxic Activity

As mentioned previously, it may be necessary, in the treatment of prophylaxis of a neoplastic growth, to administer to the patient an antidote or rescue agent. Demonstration of the efficacy in this regard of calcium leucovorin, hypoxanthine and AICAR was carried out on mouse L cells using the compounds of Examples 1 and 3. The results are as follows.

| Control | % of Control |
| --- | --- |
| Control | 100 |
| Compound of Example 1 (i) | 40 |
| Compound of Example 1 + Hypoxantine (ii) | 100 |
| Control | 100 |
| Compound of Example 1 (i) | 36 |
| Compound of Example 1 + Ca leucovorin (i) | 94 |
| Control | 100 |
| Compound of Example 3 (iii) | 37 |
| Compound Example 3 + AICAR (iv) | 100 |
| Compound of Example 3 + Hypoxanthine (ii) | 100 |
| Compound of Example 3 + Ca leucovorin (i) | 100 |

Concentrations:
(i) = $2 \times 10^{-7}$ M
(ii) = $3.7 \times 10^{-5}$ M
(iii) = $4 \times 10^{-8}$ M
(iv) = $100 \times 10^{-6}$ M From the foregoing data, it can, therefore, be concluded that each of calcium leucovorin and hypoxantine are able to reverse the cytotoxicity of the compound of Example 1 and that each of calcium leucovorin, hypoxanthine and AICAR are able to reverse the cytotoxicity of the compound of Example 3.

D. Data for Activity Against Spiroplasma citri, Sensitivity Test

Frozen broth cultures are diluted to a predetermined titre of 100 color changing units for the test. Organisms are grown in Difco PPLO broth base with added serum, glucose, phenol red, ampicillin, thallium acetate and yeast extract. Incubation is at 32° C. Incubation with varying levels of the test compound in the above medium are performed in well plates and an amount of *Spiroplasma citri* cells is added that will produce a color change by a fixed time of growth. The lowest concentration of compound that fails to produce a color change or gives a two day delay in color change indicates minimum inhibitory concentration.

The compounds of the invention included in this test and the results are as follows:

| Compound of Example | M.I.C. (μM) |
| --- | --- |
| 1 | 0.01 |
| 2 | 0.1 |
| 3 | 0.1 |

From the foregoing data, it can, therefore, be concluded that the compounds of Examples 1 to 3 are active against the mycoplasma, *Spiroplasma citri*.

What I claim is:

1. A compound of formula (I):

wherein $R^1$ is hydrogen, $C_{1-4}$ alkyl, acetyl or formyl; $R^2$ and $R^3$ are the same or different and are hydrogen or $C_{1-4}$ alkyl; $R^4$ is $NR^{11}R^{12}$; $R^{11}$, $R^{12}$, $R^5$ and $R^6$ are the same or different and are hydrogen, $C_{1-4}$ alkyl or $C_{1-12}$ acyl; $R^7$, $R^8$, $R^9$ and $R^{10}$ are the same or different and are hydrogen, halo, $C_{1-4}$ haloalkyl, $C_{1-4}$ alkyl and $C_{1-4}$ alkoxy; and n is 2, 3, 4 or 5; m is 0 or an integer from 1 to 6; or a salt thereof.

2. A compound according to claim 1, wherein $NR^1$ is NH or NCHO.

3. A compound according to claim 1, wherein $R^4$ and $NR^5R^6$ are both $NH_2$.

4. A compound according to claim 1, wherein $R^2$, $R^3$, $R^7$, $R^8$, $R^9$ and $R^{10}$ are all hydrogen.

5. A compound according to claim 1, wherein n is 2 or 3.

6. A compound according to claim 1, wherein m is 0.

7. A compound according to claim 1 which is selected from N-[4-(3-(2,4-diamino-1,6-dihydro-6-oxo-5-pyrimidinyl)propylamino]benzoyl]-L-glutamic acid,
   N-[4-[3-(2,4-diamino-1,6-dihydro-6-oxo-5-pyrimidinyl)-N-methylpropylamino]benzoyl]-L--glutamic acid,
   N-[4-[3-(2,4-diamino-1,6-dihydro-6-oxo-5-pyrimidinyl)-N-formyl-propylamino]benzoyl]-L-glutamic acid, and
   N-[4-[2-(2,4-diamino-1,6-dihydro-6-oxo-5-pyrimidinyl)ethyl-N-methylamino]benzyl]-L--glutamic acid,
   or salts thereof.

8. A pharmaceutical formulation, which comprises a compound according to claim 1, or a pharmaceutically acceptable salt thereof, and a pharmaceutically acceptable carrier therefor.

9. N-[4-(3-(2,4-diamino-1,6-dihydro-6-oxo-5-pyrimidinyl)propylamino]-benzoyl]-L-glutamic acid.

10. A pharmaceutically acceptable salt of N-[4-(3-(2,4-diamino-1,6-dihydro-6-oxo-5-pyrimidinyl)-propylamino]benzoyl]-L-glutamic acid.

11. A pharmaceutical composition comprising the compound of claim 9 and a pharmaceutically acceptable carrier therefor.

12. A pharmaceutical composition comprising the salt of claim 10 and a pharmaceutically acceptable carrier therefor.

13. The compound or salt of claim 1 in which the salt is pharmaceutically acceptable.

* * * * *